(12) United States Patent
Bi

(10) Patent No.: US 7,412,877 B1
(45) Date of Patent: Aug. 19, 2008

(54) HIGH PRESSURE VISCOMETER WITH CHAMBER PREVENTING SAMPLE CONTAMINATION

(75) Inventor: Hongfeng Bi, Houston, TX (US)

(73) Assignee: Hongfeng BI, Houston, TX (US)

( * ) Notice: Subject to any disclaimer, the term of this patent is extended or adjusted under 35 U.S.C. 154(b) by 387 days.

(21) Appl. No.: 11/257,231

(22) Filed: Oct. 24, 2005

(51) Int. Cl.
*G01N 11/14* (2006.01)

(52) U.S. Cl. .................. 73/54.28; 73/54.23; 73/54.26; 73/54.27

(58) Field of Classification Search ............ 73/54.28, 73/54.23, 54.26, 54.27
See application file for complete search history.

(56) References Cited

U.S. PATENT DOCUMENTS

| | | | |
|---|---|---|---|
| 231,367 A | 8/1880 | Smout | |
| 3,073,151 A | 1/1963 | Fann | |
| 3,239,325 A | 3/1966 | Roberson et al. | |
| 3,435,666 A | 4/1969 | Fann | |
| 4,466,276 A | 8/1984 | Ruyak et al. | |
| 4,524,611 A | 6/1985 | Richon et al. | |
| 4,534,209 A | 8/1985 | Sanders | |
| 4,630,468 A | 12/1986 | Sweet | |
| 4,633,708 A * | 1/1987 | Blommaert | 73/54.35 |
| 4,736,624 A | 4/1988 | Arnstein et al. | |
| 5,874,666 A | 2/1999 | Bishop | |
| 6,938,464 B1 * | 9/2005 | Bi | 73/54.28 |
| 6,951,127 B1 * | 10/2005 | Bi | 73/54.37 |

* cited by examiner

*Primary Examiner*—Hezron E. Williams
*Assistant Examiner*—Rodney T Frank

(57) ABSTRACT

Viscometer (80) with a rotor (51) rotatable by a coupling magnet (34) and a driving magnet (38) to shear a tested fluid thus imparting torque to a bob (30) mounted on a bob shaft (24) supported via a pair of bob shaft bearings. A spiral spring (70) restricts the rotation of bob shaft (24). Magnetometer (10) measures the angular position of a top magnet (72) connected to the top of bob shaft (24). This angular position information is further converted to the viscosity of the tested fluid.

20 Claims, 3 Drawing Sheets

HIGH PRESSURE VISCOMETER WITH CHAMBER PREVENTING SAMPLE CONTAMINATION

CROSS-REFERENCE TO RELATED APPLICATIONS

This is a division of a utility patent application "Low Maintenance High Pressure Viscometer", filed Oct. 24, 2005.

BACKGROUND

1. Field of Invention

The present invention relates to a low maintenance high pressure viscometer.

2. Description of Prior Art

In connection with the drilling of oil and gas wells, drilling fluid is commonly used to drive drill bit and bring sand and stone cuttings back to ground surface. Viscosity property of drilling fluid is critical in the drilling process. A drilling fluid with excessive viscosity would make it difficult to pump it down to bore hole, while a drilling fluid with insufficient viscosity would make it difficult to carry sand and stone cuttings back to ground surface. The viscosity property of a drilling fluid varies significantly with the change of temperature and pressure. Thus a viscometer capable of closely simulating down-hole conditions with low maintenance is of great interest. Down-hole conditions are typically from room temperature and pressure up to 40,000 psi and 600° F.

A few types of arrangements have been applied to measure the viscosity of liquids under high temperature and high pressure conditions. In U.S. Pat. No. 3,435,666, a helical spring is attached to the inside bob through a bob shaft while driving the outer cylinder. The shear force applied on the bob is proportional to the torque applied by the liquid, which is also measured by a strain gauge torque transducer. One of the drawbacks of this design is that packing 41 is required to dynamically seal the rotating tube 32. Due to the nature of the dynamical seal, it has difficulty to seal above 2,000 psi. Thus any test conditions above 2,000 psi in pressure will be difficult to achieve. In U.S. Pat. No. 4,633,708, a sealed container within a high pressure vessel is used for testing Theologically evolutive materials. One of the drawbacks of this design is that seal 12 is used to separate the test sample from outside pressurizing fluid. Measurement error due to the friction between seal 12 and shaft 14 is inevitably added. For very thick test samples such as cement this error is possibly tolerable. However, a typical drilling fluid under high temperature and pressure conditions has a typical viscosity of 10 cP to 30 cP when shear rate is around 500 1/s. This friction-induced error is too high to provide meaningful results. In U.S. Pat. No. 4,466,276, an open top slurry cup within a high pressure vessel is used to measure cement consistency. One of the drawbacks of this design is that due to the wide-open top of the slurry cup, the sample can mix with pressurization fluid easily, which leads to inaccurate results. In model 75 viscometer manufactured by Fann Instrument Company, a pair of v-shape jewel bearings is used to support a complicated bob assembly whose rotational movement is restricted by a helical spring. One of the drawbacks of this design is that the jewel bearings are fragile, easy to break, prone to wear and expensive to replace. Another drawback of this design is that helical spring assembly is generally much more complicated and spacious comparing to spiral spring assembly.

It is an object of this invention to provide a high pressure viscometer wherein viscosity is determined under conditions closely simulating down-hole conditions.

It is another object of this invention to provide a high pressure viscometer that eliminates measurement errors due to seal frictions.

It is another object of this invention to provide a viscometer that requires substantially less maintenance work yet meets industry standards of accuracy, reliability, durability, dependability, and ease of cleaning.

SUMMARY

A viscometer in accord with the present invention conveniently comprises a pressure vessel inside which a rotor is suspended and a magnetic coupling for rotating the rotor. Suspended within the rotor is a bob capable of angular motion about the longitudinal axis of the rotor. The device is constructed so that the bob and the rotor are immersed within the liquid, the viscosity of which is to be determined. The bob is suspended within the pressure vessel by a pair of low friction ball bearings and bob shaft. A spiral spring permits limited angular motion of the bob shaft. A magnet is secured on top of the bob shaft. A magnetometer located on the top of the pressure vessel senses the rotation of the magnet.

The apparatus and method of the present invention provide a way to measure the shear stress property of fluid under shear condition.

DRAWING FIGURES

Other objects, features and advantages will be apparent from the following detailed description of preferred embodiments taken in conjunction with accompanying drawing in which.

REFERENCE NUMERALS IN DRAWINGS

Figure 1:
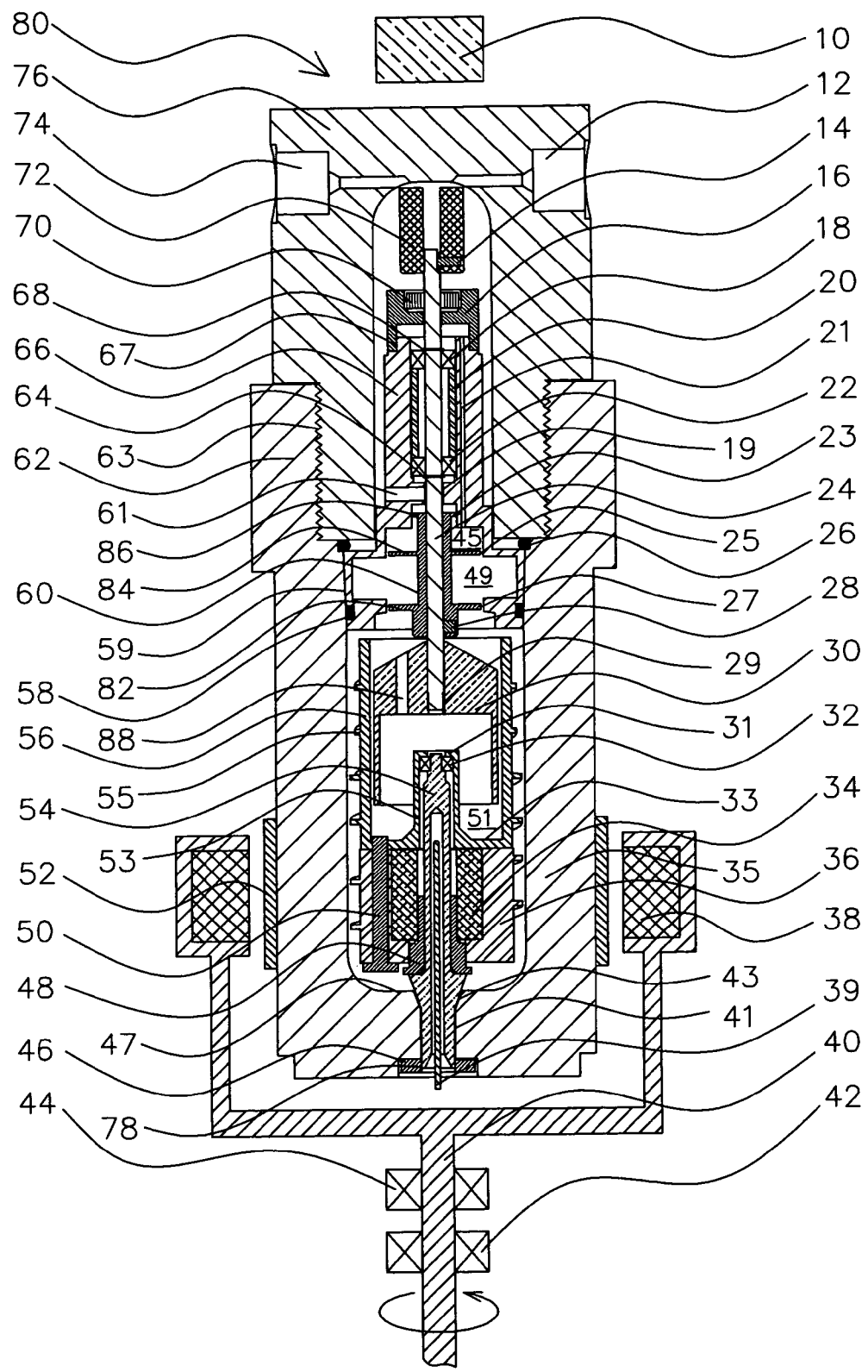
FIG. 1 is a cross-section view of a preferred embodiment of the invention.

| | |
|---|---|
| 10 magnetometer | 10A magnetometer |
| 10B magnetometer | 12 inlet |
| 12A inlet | 12B inlet |
| 13A top jewel bearing | 13B top jewel bearing |
| 14 set screw | 14A set screw |
| 14B set screw | 15A top sleeve |
| 15B top sleeve | 16 spring holder |
| 16A spring holder | 16B spring holder |
| 18 bob shaft bearing | 19 small gap |
| 19A small gap | 19B small gap |
| 20 bearing spacer | 21 sample injection hole |
| 21A sample injection hole | 21B sample injection hole |
| 22 bob shaft bearing | 23 small gap |
| 23A small gap | 23B small gap |
| 24 bob shaft | 24A bob shaft |
| 24B bob shaft | 25 small gap |
| 25A small gap | 25B small gap |
| 26 o-ring | 26A o-ring |
| 26B o-ring | 27 small gap |
| 27A small gap | 27B small gap |
| 28 set screw | 28A set screw |
| 28B set screw | 29 screw thread |
| 30 bob | 30A bob |
| 30B bob | 31 rotor inside cap |
| 31A rotor inside cap | 31B rotor inside cap |
| 32 support bearing | 32A support bearing |
| 32B support bearing | 33 rotor bottom |
| 33A rotor bottom | 33B rotor bottom |

-continued

| | |
|---|---|
| 34 coupling magnet | 34A coupling magnet |
| 34B coupling magnet | 35 cell wall |
| 35A cell wall | 35B cell wall |
| 36 magnet holder | 36A magnet holder |
| 36B magnet holder | 38 driving magnet |
| 38A driving magnet | 38B driving magnet |
| 39 thermal couple | 39A thermal couple |
| 39B thermal couple | 40 magnet mount |
| 40A magnet mount | 40B magnet mount |
| 41 straight bore | 41A straight bore |
| 41B straight bore | 42 bearing |
| 42A bearing | 42B bearing |
| 43 conical surface | 43A conical surface |
| 43B conical surface | 44 bearing |
| 44A bearing | 44B bearing |
| 45 chamber | 46 lock nut |
| 46A lock nut | 46B lock nut |
| 47 cell bottom | 47A cell bottom |
| 47B cell bottom | 48 bushing |
| 48A bushing | 48B bushing |
| 49 chamber | 49A chamber |
| 49B chamber | 50 screw |
| 50A screw | 50B screw |
| 51 rotor | 51A rotor |
| 51B rotor | 52 heater |
| 52A heater | 52B heater |
| 53 rotor inside wall | 53A rotor inside wall |
| 53B rotor inside wall | 54 pivot |
| 54A pivot | 54B pivot |
| 55 fin | 55A fin |
| 55B fin | 56 rotor outside wall |
| 56A rotor outside wall | 56B rotor outside wall |
| 57A or 57B bottom jewel bearing | 58 o-ring |
| 58A o-ring | 59 conical surface |
| 59A conical surface | 60 anti mixer |
| 60A anti mixer | 60B anti mixer |
| 61 venting hole | 61A venting hole |
| 62 cell body | 62A cell body |
| 62B cell body | 63 screw thread |
| 63A screw thread | 63B screw thread |
| 64 snap ring | 66 bearing holder |
| 66A bearing holder | 66B cell coupling |
| 67 flat | 67A flat |
| 67B flat | 68 snap ring |
| 70 spiral spring | 70A spiral spring |
| 70B spiral spring | 72 top magnet |
| 72A top magnet | 72B top magnet |
| 74 outlet | 74A outlet |
| 74B outlet | 76 cell cap |
| 76A cell cap | 76B cell cap |
| 78 thread | 80 viscometer |
| 80A viscometer | 80B viscometer |
| 82 anti mixer bottom fin | 82A anti mixer bottom fin |
| 82B anti mixer bottom fin | 84 anti mixer middle fin |
| 84A anti mixer middle fin | 84B anti mixer middle fin |
| 86 anti mixer top fin | 86A anti mixer top fin |
| 86B anti mixer top fin | 88 bob vent |
| 90A needle pin | 90B needle pin |

DESCRIPTION

FIG. 1—Preferred Embodiment

FIG. 1 is a cross-section view of a viscometer 80 with a cell body 62 and a cell cap 76. Cell body 62 is detachable from cell cap 76 via a screw thread 63. An o-ring 26 assures against the escape of fluid through screw thread 63. Inside of cell body 62 and below screw thread 63 is a conical surface 59 with reduced diameter, below which a cylindrical cell wall 35 extends downward to a cell bottom 47. A tapered hole with a conical surface 43 and a straight bore 41 is located in the center of cell bottom 47. A pivot 54, which is secured to cell bottom 47 by a lock nut 46 through a thread 78, is seated into said tapered hole on conical surface 43. Lock nut 46 is tightened to provide initial seal on conical surface 41 between cell bottom 47 and pivot 54. A thermal couple 39 is inserted into the center of pivot 54. Radially outward of the outer surface of pivot 54 is a bushing 48. Bushing 48 is made of Rulon, Teflon or equivalent plastics. A magnet holder 36 and a coupling magnet 34 are positioned radially outward of bushing 48. A screw 50 secures magnet holder 36 and coupling magnet 34 to the bottom of a rotor 51. Rotor 51 consists of a cylindrical rotor outside wall 56, a disc shape rotor bottom 33, a hollow cylindrical rotor inside wall 53 and a rotor inside cap 31. A fin 55 extruded on the outer surface of rotor outside wall 56 provides better agitation of sample during measurement. A support bearing 32 provides vertical support of the assembly of rotor 51, magnet holder 36 and coupling magnet 34, which can rotate freely on the same central axis of pivot 54.

A bearing holder 66 consists of a conical section and two different outside diameter sections. The outer surface of the conical section of bearing holder 66 mates inside conical surface 59 of cell body 62. An o-ring 58 provides liquid-tight seal on conical surface 59. A bob shaft 24 passes through the center of bearing holder 66 and rotationally supported by a bob shaft bearing 18, a bob shaft bearing 22, a bearing spacer 20, a snap ring 68 and a snap ring 64. An anti-mixer 60 is attached on bob shaft 24 by a set screw 28. Anti mixer 60 consists of an anti mixer bottom fin 82, an anti mixer middle fin 84, an anti mixer top fin 86 and a cylindrical shell that connects these three fins together. Bearing holder 66 has various inside diameter bore sections so that a small gap 23, a small gap 25 and a small gap 27 are formed between the outside diameter of those anti mixer fins and those inside bore sections of bearing holder 66. Furthermore, a chamber 45 is formed between anti mixer top fin 86 and anti mixer middle fin 84 and a chamber 49 is formed between anti mixer middle fin 84 and anti mixer bottom fin 82. A bob 30 is crewed on the bottom of bob shaft 24 via a screw thread 29. A bob vent 88 is provide along the axial direction of bob 30 connecting the inside vacancy of bob 30 to its top.

A machined flat 67 is provided on the top of bearing holder 66. Mating and resting on flat 67 is a spring holder 16. A spiral spring 70 is placed in the center of spring holder 16 so that the outside lead of spiral spring 70 is fixed to the inside counter bore of spring holder 16 and the inside lead of spiral spring 70 is fixed to bob shaft 24 with any conventional means. A horseshoe type top magnet 72 is fixed to the top of bob shaft 24 with a set screw 14. Additionally, a sample injection hole 21 channels from the top of bearing holder 66 to chamber 45. A venting hole 61 connects outer surface of bearing holder 66 to a small gap 19 between bob shaft 240D and bearing holder 66 ID.

An inlet 12 and an outlet 74 provide ports for applying and releasing pressure. A magnetometer 10 located on the top of cell cap 76 can measure the rotational displacement of top magnet 72.

A magnet mount 40 is rotationally supported on the outside of cell body 62 by a bearing 42 and a bearing 44. Magnet mount 40 can be rotated by any conventionally means such as gear box or motor. A pair of driving magnet 38 is mounted on magnet mount 40 at considerably the same level where coupling magnet 34 is mounted inside of the cell body 62.

OPERATION

FIG. 1—Preferred Embodiment

Pivot 54 is secured to cell body 62 by lock nut 46 and can be cleaned together with cell body 62. During installation, screw 50 holds magnet holder 36, coupling magnet 34 and rotor 51 together. Bushing 48 is pushed into the bottom of magnet holder 36. This said subassembly is dropped into cell body 62 and rotationally supported by pivot 54. Test sample is poured into cell body 62 so that sample surface just submerges the top of rotor 51.

Holding bob shaft 24 in hand, install bob shaft bearing 18, bearing spacer 20, bob shaft bearing 22, snap ring 68 and snap ring 64 onto bob shaft 24. Then vertically insert this subassembly into bearing holder 66. Next install spring holder 16 and spiral spring 70 onto the top of bearing holder 66. Top magnet 72 is secured to the top of bob shaft 24 thereafter. Slide anti mixer 60 onto bob shaft 24 from bottom of bob shaft 24 and secure it at the position as shown in FIG. 1 with set screw 28. Bob 30 is finally screwed onto bob shaft 24 bottom via screw thread 29. Install o-ring 58 onto the outer surface of bearing holder 66. Then vertically push this bob shaft holder assembly down into cell body 62 slowly.

During pushing down this bob shaft holder assembly, air trapped inside of bob 30 is vented through bob vent 88. Bob 30 also expels the sample fluid causing sample fluid level to rise. This expelled volume is stopped by o-ring 58 and can only cause sample fluid level to rise inside of bearing holder 66. Consequently, chamber 49 is partially or totally filled with sample fluid after bearing holder assembly is total seated down engaging with cell body 62 on conical surface 59. A syringe is used to inject additional sample fluid through sample injection hole 21 to bring sample fluid level up so that sample fluid would totally fill up chamber 49 and chamber 45. Finally screw down cell cap 76 with o-ring 26 in place. Pump pressurization fluid from inlet 12 until all air inside of pressure vessel is expelled out through outlet 74. Sample testing pressure can be raised by pumping more pressurization fluid into pressure vessel or releasing some pressurization fluid from pressure vessel.

It is very important to have rotor 51 and bob 30 concentrically aligned. Conical surface 59 is machined with high precision to ensure bob 30 is concentrically aligned with rotor 51. This conical surface 59 also significantly simplifies the installation process since no addition adjustment or screw turning is required to ensure the good concentricity between rotor 51 and bob 30.

A motor or gearbox drives magnet mount 40 to rotate carrying driving magnet 38. A heater 52 heats up cell body 62 while thermal couple 39 provides temperature feedback for temperature control. Due to the magnetic coupling between driving magnet 38 and coupling magnet 34, rotor 51 rotates at the same revolving speed as magnet mount 40 does. Because the viscosity of tested sample, a torque is generated on bob 30 causing it to rotate. Because of spiral spring 70, the rotation angle of bob shaft 24 is roughly proportional to the torque applied on bob 30. Magnetometer 10 picks up the rotation angle of top magnet 72 which rotates with bob shaft 24. The rotation angle in turn can be used to calculate the viscosity of tested sample.

One of the drawbacks of most liquid pressurized viscometers is the mixing between tested sample and pressurization fluid. If a seal is provided between pressurization fluid and tested sample, the seal will induce friction error causing inaccurate measurement. If pressurization fluid is allowed to contact tested sample directly, pressurization fluid will mix with tested sample because of stirring and compressibility of tested sample.

In current invention, when pressurization fluid is applied, the sample fluid level is pushed down due to the compressibility of tested sample. Thus initial sample fluid inside of chamber 45 goes down to chamber 49 through small gap 25, and some of the initial sample fluid inside of chamber 49 goes down to the lower measurement zone through small gap 27. However, chamber 45 and chamber 49 are large enough so that at maximum rated pressure, chamber 49 is still at least half filled with sample fluid. This ensures the accuracy of the measurement because measurement zone below anti mixer bottom fin 82 is always totally filled with sample fluid.

Additionally, because anti mixer bottom fin 82 separates lower measurement zone and chamber 49, fluid inside of chamber 49 is relatively static. Thus no stirring could cause the mixing between pressurization fluid and tested sample if the interface between pressurization fluid and tested sample is inside of chamber 49.

The pressurization fluid should be chosen carefully. This pressurization fluid should not spontaneously dissolve into or mix with the tested sample, and should have a specific gravity lower than the specific gravity of the sample. Pressurization fluid communicates pressure with sample fluid through venting hole 61 and small gap 23 while keeping bob shaft bearing 18 and bob shaft bearing 22 submerged. Because pressurization fluid is generally a clean, nonabrasive liquid, this ensures bob shaft bearing 18 and bob shaft bearing 22 rotate freely and have long working life span. If conventional type of bearings, such as roller bearing, ball bearing and spherical bearing, are used in a comparative viscometer without mechanism preventing sample mixing with pressurization fluid, those bearings will quickly stop working properly, normally with excessive drag, because tested sample is normally filled with a lot of fine solid contents.

DESCRIPTION

Figure 2:
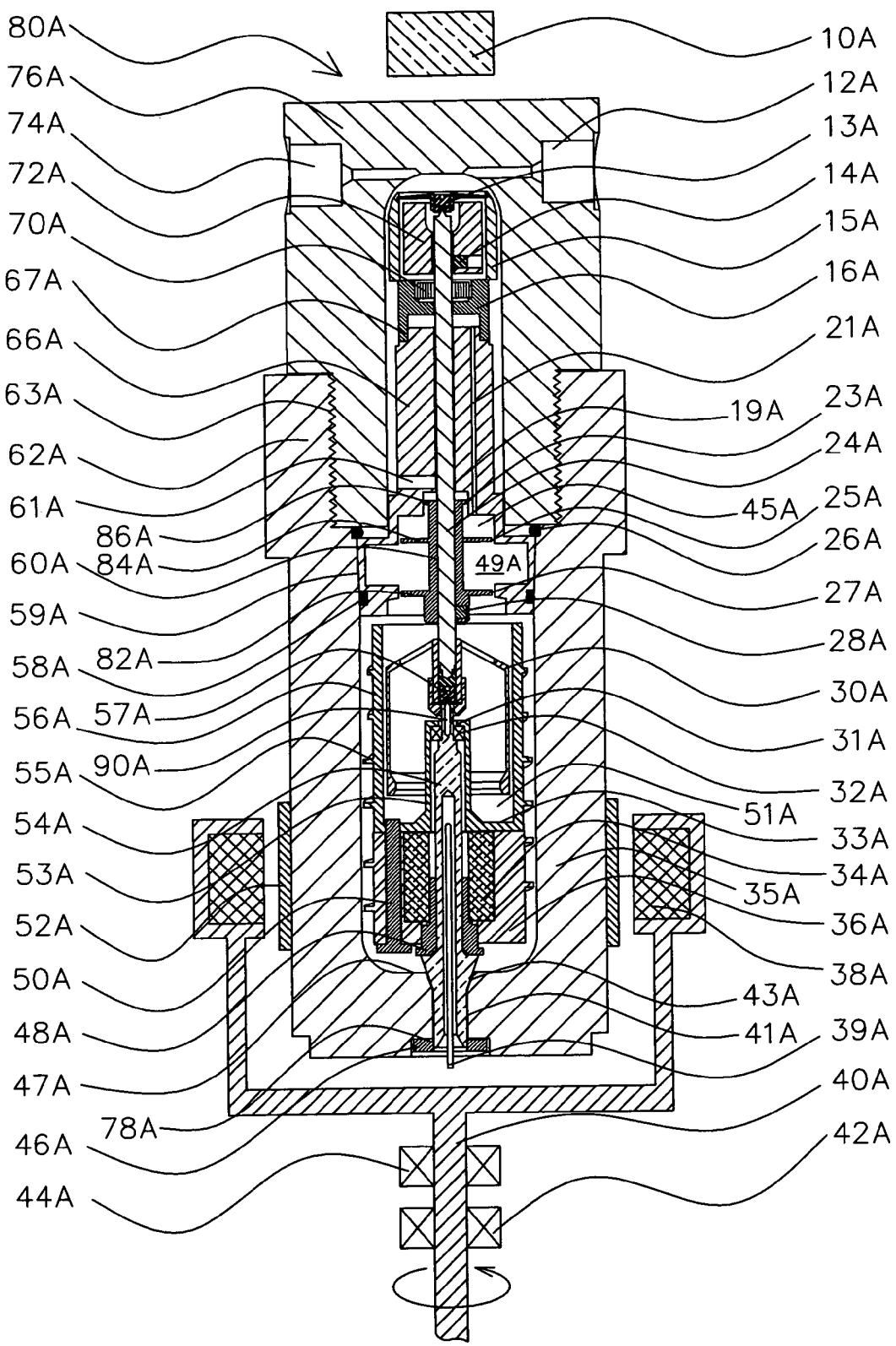
FIG. 2 is an alternative embodiment with jewel bearings and conical support.

FIG. 2—An Alternative Embodiment with Jewel Bearings and Conical Support

FIG. 2 is a cross-section view of a viscometer 80A with a cell body 62A and a cell cap 76A. Cell body 62A is detachable from cell cap 76A via a screw thread 63A. An o-ring 26A assures against escape of fluid through screw thread 63A. Inside of cell body 62A and below screw thread 63A is a conical surface 59A with reduced diameter, below which a cylindrical cell wall 35A extends downward to a cell bottom 47A. A tapered hole with a conical surface 43A and a straight bore 41A is located in the center of cell bottom 47A. A pivot 54A, which is secured to cell bottom 47A by a lock nut 46A through a thread 78A, is seated into said tapered hole on conical surface 43A. Lock nut 46A is tightened to provide initial seal on conical surface 41A between cell bottom 47A and pivot 54A. A thermal couple 39A is inserted into the center of pivot 54A. Radially outward of the outer surface of pivot 54A is a bushing 48A. Bushing 48A is made of Rulon, Teflon or equivalent plastics. A magnet holder 36A and a coupling magnet 34A are positioned radially outward of bushing 48A. A screw 50A secures magnet holder 36A and coupling magnet 34A to the bottom of a rotor 51A. Rotor 51A consists of a cylindrical rotor outside wall 56A, a disc shape rotor bottom 33A, a hollow cylindrical rotor inside wall 53A and a rotor inside cap 31A. A fin 55A extruded on the outer surface of rotor outside wall 56A provides better agitation of sample during measurement. A support bearing 32A provides vertical support of the assembly of rotor 51A, magnet holder 36A and coupling magnet 34A, which can rotate freely on the same central axis of pivot 54A.

A bearing holder 66A consists of a conical section and two different outside diameter sections. The outer surface of the conical section of bearing holder 66A mates inside conical surface 59A of cell body 62A. An o-ring 58A provides liquid-tight seal on conical surface 59A. A bob shaft 24A passes through the center of bearing holder 66A while not in contact with its inside bore directly. A machined flat 67A is provided on the top of bearing holder 66A. Mating and resting on flat 67A is a spring holder 16A. A spiral spring 70A is placed in the center of spring holder 16A so that the outside lead of spiral spring 70A is fixed to the inside counter bore of spring holder 16A and the inside lead of spiral spring 70A is fixed to bob shaft 24A with any conventional means.

A needle pin 90A has its lower portion fixed on the top of pivot 54A. Resting on the top of needle pin 90A is a bottom jewel bearing 57A secured to the bottom of bob shaft 24A. Resting on top of spring holder 16A is a top sleeve 15A, on which a top jewel bearing 13A is mounted. The tip of bob shaft 24 is in contact with top jewel bearing 13A. Thus bob shaft 24 is rotationally supported by bottom jewel bearing 57A and top jewel bearing 13A. Also secured to the bottom of bob shaft 24A is a bob 30A.

A horseshoe type top magnet 72A is also fixed to the top of bob shaft 24A with a set screw 14A.

An anti-mixer 60A is attached on bob shaft 24A by a set screw 28A. Anti mixer 60A consists of an anti mixer bottom fin 82A, an anti mixer middle fin 84A, an anti mixer top fin 86A and a cylindrical shell that connects these three fins together. Bearing holder 66A has various inside diameter bore sections so that a small gap 23A, a small gap 25A and a small gap 27A are formed between the outside diameter of those anti mixer fins and those inside bore sections of bearing holder 66A. Furthermore, a chamber 45A is formed between anti mixer top fin 86A and anti mixer middle fin 84A and a chamber 49A is formed between anti mixer middle fin 84A and anti mixer bottom fin 82A.

Additionally, a sample injection hole 21A channels from the top of bearing holder 66A to chamber 45A. A venting hole 61A connects outer surface of bearing holder 66A to a small gap 19A between bob shaft 24A OD and bearing holder 66A ID.

An inlet 12A and an outlet 74A provide ports for applying and releasing pressure. A magnetometer 10A located on the top of cell cap 76A can measure the rotational displacement of top magnet 72A.

A magnet mount 40A is rotationally supported on the outside of cell body 62A by a bearing 42A and a bearing 44A. Magnet mount 40A can be rotated by any conventionally means such as gear box or motor. A pair of driving magnet 38A is mounted on magnet mount 40A at considerably the same level where coupling magnet 34A is mounted inside of the cell body 62A.

OPERATION

FIG. 2—An Alternative Embodiment with Jewel Bearings and Conical Support

Pivot 54A is left on cell body 62A secured by lock nut 46A between tests and can be cleaned together with cell body 62A. During installation, screw 50A holds magnet holder 36A, coupling magnet 34A and rotor 51A together. Bushing 48A is pushed into the bottom of magnet holder 36A. This said subassembly is dropped into cell body 62A and rotationally supported by pivot 54A. Test sample is poured into cell body 62A so that sample surface just submerges the top of rotor 51A.

Insert bob shaft 24A into bearing holder 66A. Next install spring holder 16A and spiral spring 70A onto the top of bearing holder 66A. Top magnet 72A is secured to the top of bob shaft 24A thereafter. Slide anti mixer 60A onto bob shaft 24A from bottom of bob shaft 24A and secure it at the position as shown in FIG. 2 with set screw 28A. Bob 30A is finally screwed onto bob shaft 24A bottom via screw thread 29A. Install o-ring 58A onto the outer surface of bearing holder 66A. Then vertically push this bob shaft holder assembly down into cell body 62A slowly.

During pushing down this bob shaft holder assembly, bob 30A expels the sample fluid causing sample fluid level to rise. This expelled volume is stopped by o-ring 58A and can only cause sample fluid level to rise inside of bearing holder 66A. Consequently, chamber 49A is partially or totally filled with sample fluid after bearing holder assembly is total seated down engaging with cell body 62A on conical surface 59A. A syringe is used to inject additional sample fluid through small injection hole 21A to bring sample fluid level up so that sample fluid would totally fill up chamber 49A and chamber 45A. Then place top sleeve 15A on top of spring holder 16A so that bob shaft 24A is centered by top jewel bearing 13A. Finally screw down cell cap 76A with o-ring 26A in place. Pump pressurization fluid from inlet 12A until all air inside of pressure vessel is expelled out through outlet 74A. Sample testing pressure can be raised by pumping more pressurization fluid into pressure vessel or releasing some pressurization fluid from pressure vessel.

A motor or gearbox drives magnet mount 40A to rotate carrying driving magnet 38A. A heater 52A heats up cell body 62A while thermal couple 39A provides temperature feedback for temperature control. Due to the magnetic coupling between driving magnet 38A and coupling magnet 34A, rotor 51A rotates at the same revolving speed as magnet mount 40A does. Because the viscosity of tested sample, a torque is generated on bob 30A causing it to rotate. Because of spiral spring 70A, the rotation angle of bob shaft 24A is roughly proportional to the torque applied on bob 30A. Magnetometer 10A picks up the rotation angle of top magnet 72A which rotates with bob shaft 24A. The rotation angle in turn can be used to calculate the viscosity of tested sample.

In this embodiment, when pressurization fluid is applied, the sample fluid level is pushed down due to the compressibility of tested sample. Thus initial sample fluid inside of chamber 45A goes down to chamber 49A through small gap 25A, and some of the initial sample fluid inside of chamber 49A goes down to the lower measurement zone through small gap 27A. However, chamber 45A and chamber 49A are large enough so that at maximum rated pressure, chamber 49A is still at least half filled with sample fluid. This ensures the accuracy of the measurement because measurement zone below anti mixer bottom fin 82A is always totally filled with sample fluid.

DESCRIPTION

Figure 3:
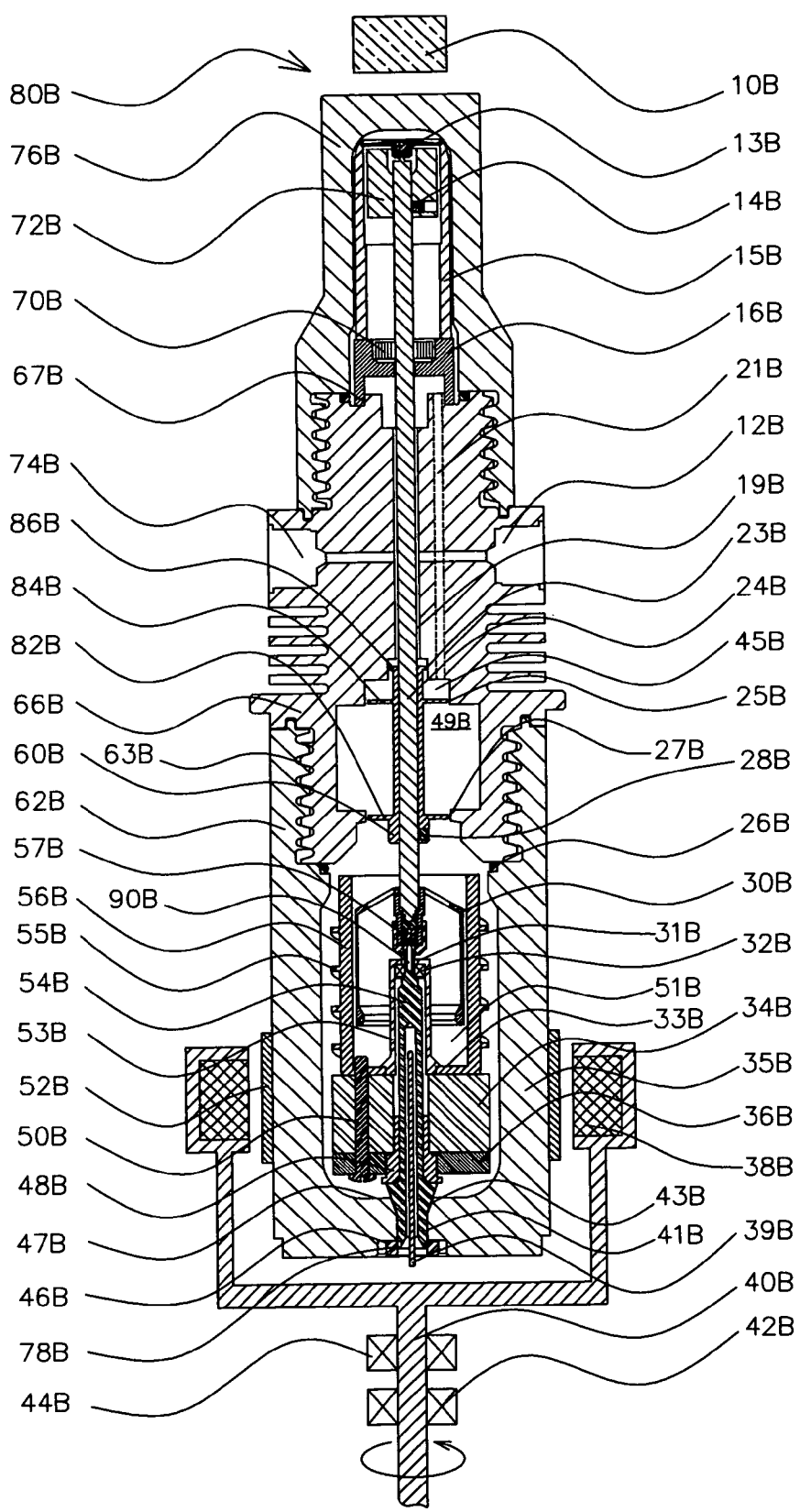
FIG. 3 is another alternative embodiment with jewel bearings and three-piece pressure vessel configuration.

FIG. 3—An Alternative Embodiment with Jewel Bearings and Three-Piece Pressure Vessel Configuration FIG. 3 is a cross-section view of a viscometer 80B with a cell body 62B, a cell coupling 66B and a cell cap 76B. Cell body 62B is detachable from cell coupling 66B via a screw thread 63B and cell cap 76B is screwed on top of cell coupling 66B. An o-ring 26B assures against escape of fluid through screw thread 63B. Inside of cell body 62 and below screw thread 63 is a conical surface 59B with reduced diameter, below which a cylindrical cell wall 35B extends downward to a cell bottom 47B. A tapered hole with a conical surface 43B and a straight bore 41B is located in the center of cell bottom 47B. A pivot 54B, which is secured to cell bottom 47B by a lock nut 46B through a thread 78B, is seated into said tapered hole on conical surface 43B. Lock nut 46B is tightened to provide initial seal on conical surface 41B between cell bottom 47B and pivot 54B. A thermal couple 39B is inserted into the center of pivot 54B. Radially outward of the outer surface of pivot 54B is a bushing 48B. Bushing 48B is made of Rulon, Teflon or equivalent plastics. A magnet holder 36B and a coupling magnet 34B are radially positioned outward of bushing 48B. A screw 50B secures magnet holder 36B and coupling magnet 34B to the bottom of a rotor 51B. Rotor 51B consists of a cylindrical rotor outside wall 56B, a disc shape rotor bottom 33B, a hollow cylindrical rotor inside wall 53B and a rotor inside cap 31B. A fin 55B extruded on the outer surface of rotor outside wall 56B provides better agitation of sample during measurement. A support bearing 32B provides vertical support of the assembly of rotor 51B, magnet holder 36B and coupling magnet 34B, which can rotate freely on the same central axis of pivot 54B.

A bob shaft 24B passes through the center of cell coupling 66B while not in contact with its inside bore directly. A machined flat 67B is provided on the top of cell coupling 66B. Mating and resting on flat 67B is a spring holder 16B. A spiral spring 70B is placed in the center of spring holder 16B so that the outside lead of spiral spring 70B is fixed to the inside counter bore of spring holder 16B and the inside lead of spiral spring 70B is fixed to bob shaft 24B with any conventional means.

A needle pin 90B has its lower portion fixed on the top of pivot 54B. Resting on the top of needle pin 90B is a bottom jewel bearing 57B secured to the bottom of bob shaft 24B. Resting on top of spring holder 16B is a top sleeve 15B, on which a top jewel bearing 13B is mounted. The tip of bob shaft 24 is in contact with top jewel bearing 13B. Thus bob shaft 24B is rotationally supported by bottom jewel bearing 57B and top jewel bearing 13B. Also secured to the bottom of bob shaft 24B is a bob 30B.

A horseshoe type top magnet 72B is also fixed to the top of bob shaft 24B with a set screw 14B.

An anti-mixer 60B is attached on bob shaft 24B by a set screw 28B. Anti mixer 60B consists of an anti mixer bottom fin 82B, an anti mixer middle fin 84B, an anti mixer top fin 86B and a cylindrical shell that connects these three fins together. Cell coupling 66B has various inside diameter bore sections so that a small gap 23B, a small gap 25B and a small gap 27B are formed between the outside diameter of those anti mixer fins and those inside bore sections of cell coupling 66B. Furthermore, a chamber 45B is formed between anti mixer top fin 86B and anti mixer middle fin 84B and a chamber 49B is formed between anti mixer middle fin 84B and anti mixer bottom fin 82B.

Additionally, a sample injection hole 21B channels from the top of cell coupling 66B to chamber 45B.

An inlet 12B and an outlet 74B provide ports for applying and releasing pressure. A magnetometer 10B located on the top of cell cap 76B can measure the rotational displacement of top magnet 72B.

A magnet mount 40B is rotationally supported on the outside of cell body 62B by a bearing 42B and a bearing 44B. Magnet mount 40B can be rotated by any conventionally means such as gear box or motor. A pair of driving magnet 38B is mounted on magnet mount 40B at considerably the same level where coupling magnet 34B is mounted inside of the cell body 62B.

OPERATION

FIG. 3—An Alternative Embodiment with Jewel Bearings and Three-Piece Pressure Vessel Configuration Pivot 54B is left on cell body 62B secured by lock nut 46B between tests and can be cleaned together with cell body 62B. During installation, screw 50B holds magnet holder 36B, coupling magnet 34B and rotor 51B together. Bushing 48B is pushed into the bottom of magnet holder 36B. This said subassembly is dropped into cell body 62B and rotationally supported by pivot 54B. Test sample is poured into cell body 62B so that sample surface just submerges the top of rotor 51B.

Secure anti mixer 60B to bob shaft 24B by tightening set screw 28B. Insert bob shaft 24B into cell coupling 66B from bottom. Next install spring holder 16B and spiral spring 70B onto the top of cell coupling 66B. Top magnet 72B is secured to the top of bob shaft 24B thereafter. Bob 30B is screwed onto bob shaft 24B bottom via screw thread 29B thereafter. Then vertically screw on cell body 62B to cell coupling 66B.

During screwing on cell body 62B, bob 30B expels the sample fluid causing sample fluid level to rise. A syringe is used to inject additional sample fluid through small injection hole 21B to bring sample fluid level up so that sample fluid would totally fill up chamber 49B and chamber 45B. Then place top sleeve 15B on top of spring holder 16B so that bob shaft 24B is centered by top jewel bearing 13B. Finally screw down cell cap 76B onto cell coupling 66B. Pump pressurization fluid from inlet 12B. Sample testing pressure can be raised by pumping more pressurization fluid into pressure vessel through inlet 12 or releasing some pressurization fluid from pressure vessel through 74B outlet.

A motor or gearbox drives magnet mount 40B to rotate carrying driving magnet 38B. A heater 52B heats up cell body 62B while thermal couple 39B provides temperature feedback for temperature control. Due to the magnetic coupling between driving magnet 38B and coupling magnet 34B, rotor 51B rotates at the same revolving speed as magnet mount 40B does. Because the viscosity of tested sample, a torque is generated on bob 30B causing it to rotate. Because of spiral spring 70B, the rotation angle of bob shaft 24B is roughly proportional to the torque applied on bob 30B. Magnetometer 10B picks up the rotation angle of top magnet 72B which rotates with bob shaft 24B. The rotation angle in turn can be used to calculate the viscosity of tested sample.

In this embodiment, when pressurization fluid is applied, the sample fluid level is pushed down due to the compressibility of tested sample. Thus initial sample fluid inside of chamber 45B goes down to chamber 49B through small gap 25B, and some of the initial sample fluid inside of chamber 49B goes down to the lower measurement zone through small gap 27B. However, chamber 45B and chamber 49B are large enough so that at maximum rated pressure, chamber 49B is still at least half filled with sample fluid. This ensures the accuracy of the measurement because measurement zone below anti mixer bottom fin 82B is always totally filled with sample fluid.

RAMIFICATIONS

It is not necessary to have both chamber 45 and chamber 49. With just chamber 45 or chamber 49 and sufficient volume, pressurization fluid and test sample can still be separated well.

Bob shaft 24 and anti-mixer 60 could be combined as one piece.

Anti mixer 60 does not have to be designed as shown in FIG. 1. Anti mixer top fin 86, anti mixer middle fin 84 and anti mixer bottom fin 82 could be removed. Then just add washer shaped fins having their roots attached to the inside diameter of bearing holder 66. The ID of said washer shaped fins should not contact bob shaft 24 while having small gaps similar to gap 25 and gap 27 to bob shaft 24.

By changing bearing holder 66 inside diameter and bob shaft 24 outside diameter, anti mixer 60 could be eliminated while viscosity 80 could still prevent mixing between pressurization fluid and test sample. For example, in viscometer 80, anti mixer 60 is removed and bob shaft 24 is designed so that axially along original bob shaft 24 from anti mixer top fin 86 to anti mixer bottom fin 82, bob shaft has an OD same as the original anti mixer top fin 86OD. As long as either chamber 45 or chamber 49 is still formed and communicates pressure from top to bottom in substantially reduced openings such as gap 25 and gap 27, viscometer 80 could still prevent mixing between pressurization fluid and test sample.

Another simpler way to form chamber 49 is removing the enlarged inside bore section of bearing holder 66 from anti mixer top fin 86 to anti mixer bottom fin 82. As long as chamber 49 is large enough, viscometer 80 could still prevent mixing between pressurization fluid and test sample.

By providing an enlarged chamber such as chamber 45 or chamber 49, and reduced openings for said enlarged chamber such as gap 25 and gap 27, this configuration can be applied to other applications than viscometers to reducing the mixing of test sample and pressurization fluid. Other applications could be consistometer, capillary rheometer, core flow tester, etc.

Bob 30 does not have to be cylindrical shape. It could be a blade, frame or any geometry shape.

Bob shaft bearing 18 and bob shaft bearing 22 could be combined as one needle bearing or equivalent bearing with low friction.

Rotor 51 does not have to be driven with a magnetic coupling across cell body 62. Rotor 51 could be driven to rotate with any means such as directly driven at the bottom of the cell body with dynamic seal, etc.

Spiral spring 70 could be helical spring or other types of equivalent resilient mechanism.

There are many other ways to measure the angular displacement of bob shaft 24. For example, in preferred embodiment viscometer 80, top magnet 72 and magnetometer 10 can be replaced with a pair of concentrically mounted electrical stator and rotor to measure the rotation of bob shaft 24. Additionally, top magnet 72 and magnetometer 10 can be replaced with an encoder to measure the rotation of bob shaft 24. A potentiometer and a brush attached to bob shaft 24 could measure the rotation as well.

Alternatively, a metal arm or wiper which rotates with bob shaft 10, and a wire-wound conductance transducer which is mounted directly or indirectly on bearing holder 66 or cell cap 76, can also be used to measure the rotation of bob shaft 24 by measuring the conductance change in the wire-wound coil.

Viscometer 80 can also be reduced to simpler construction for non-pressurized viscometer applications. It can be accomplished by removing sealing related components, such as all o-rings etc. In non-pressurized application, sample cups can have open bottoms, and the lower part of sample cups can be immersed into a liquid—the liquid's viscosity to be measured.

CONCLUSION, AND SCOPE

Accordingly, the reader will see that this invention can be used to construct a high pressure viscometer with accurate measurement easily. The simple configuration enables simple operation procedure and low maintenance.

Objects and Advantages

From the description above, a number of advantages of my viscometer become evident:
  (a) Due to conventional low friction ball bearings design, current invention substantially reduces operation cost comparing to jewel bearing designs. It had been unsuccessful to use conventional ball bearings in liquid pressurized high pressure viscometer because any fine solids in tested sample would cause low friction ball bearings to fail. Also because ball bearings are much durable than jewel bearings, maintenance task is reduced significantly.
  (b) Totally eliminate the measurement error because of sample mixing with pressurization fluid in a comparative viscometer.
  (c) Very conveniently isolate all electrical component from pressurized zone thus reducing maintenance work.
  (d) Very compact design by using small size spiral spring.
  (e) Extremely simple installation and disassembly procedures due to conical bearing holder design while maintaining high concentricity between bob and rotor.

Further objects and advantages of my invention will become apparent from a consideration of the drawings and ensuing description.

The invention claimed is:
1. A pressurized device comprising:
  (a) a pressure vessel within which is vertically disposed at least one top section filled with a pressurization fluid of a first density and at least one lower section filled with a test sample of a second density,
  (b) an enlarged chamber with reduced openings positioned between the at least one top section and the at least one bottom section for communicating pressure with said top section and said lower section within said pressure vessel,
  (c) whereby said pressurization fluid would not mix with said test sample because of the nature of their density difference.

2. The device of claim 1 wherein said pressurized device is a viscometer.

3. The device of claim 1 wherein said pressurized device is a consistometer.

4. Viscometer comprising:
  (a) a pressure vessel within which at least one top section filled with a pressurization fluid of a first density,
  (b) within said pressure vessel a rotor which is driven to rotate while contacting with a sample liquid of a second density to be measured,
  (c) means for driving said rotor to rotate located in at least one bottom section,
  (d) a bob within said rotor,
  (e) an enlarged chamber with reduced openings positioned between the at least one top section and the at least one bottom section for communicating pressure located above said bob,
  (f) whereby said pressurization fluid would not mix with said sample liquid because of the nature of their density difference.

5. A viscometer according to claim 4 further comprising a bearing means for rotationally suspending said bob.

6. The viscometer of claim 5 wherein said bearing means are low friction ball bearings or roller bearings.

7. The viscometer of claim 5 wherein said bearing means are low friction jewel bearings.

8. A viscometer according to claim 5 further comprising a spring means restricting the rotation of said bob.

9. The viscometer of claim 8 wherein said spring means is a spiral spring.

10. The viscometer of claim 8 wherein said spring means is a helical spring.

11. A viscometer according to claim 8 further comprising means for directly or indirectly sensing the rotation of said bob.

12. The viscometer of claim 11 wherein said means for directly or indirectly sensing the rotation of said bob consist of a magnet and a magnetometer.

13. The viscometer of claim 11 wherein said means for directly or indirectly sensing the rotation of said bob consist of a potentiometer and a brush.

14. The viscometer of claim 4 wherein said means for driving said rotor to rotate is a magnetic coupling across said pressure vessel wall.

15. The viscometer of claim 4 wherein said bob is cylindrical shape.

16. A viscometer according to claim 4 further comprising a bob suspension means comprising at least one conical outer surface part mating another conical surface which directly or indirectly associated to said pressure vessel.

17. The viscometer of claim 4 wherein said enlarged chamber formed by at least two washer shaped fins disposed parallelly along the axial direction that said bob rotates.

18. The viscometer of claim 17 wherein said two washer shaped fins have their inside diameters connected to a bob shaft which suspends said bob and said two washer shaped fins are not directly in contact with other static mechanical components.

19. The viscometer of claim 17 wherein said two parallel washer shaped fins having their outside diameters connected to a bob suspension means while their inside diameters separated from said bob and any component that rotates together with said bob.

20. A viscometer according to claim 4 further comprising a bob suspension means comprising at least one conical outer surface part mating another conical surface which directly or indirectly associated to said pressure vessel.

* * * * *